United States Patent [19]

Takata et al.

[11] Patent Number: 5,219,337
[45] Date of Patent: Jun. 15, 1993

[54] LIQUID CHEMICALS INJECTOR HAVING A LIQUID CONTAINER AND CATHETER

[75] Inventors: Junichi Takata; Sigeru Yamana, both of Toyama, Japan

[73] Assignees: Hashin Kasei Kogyo K.K.; Ohta Pharmaceutical Co., Ltd., both of Japan

[21] Appl. No.: 737,742

[22] Filed: Jul. 30, 1991

[30] Foreign Application Priority Data

Aug. 1, 1990 [JP] Japan .................................. 2-81967

[51] Int. Cl.[5] ............................................. A61M 5/178
[52] U.S. Cl. .................................... 604/185; 604/200; 604/213; 604/257; 222/541
[58] Field of Search ............................ 222/494–497, 222/507, 541; 604/181, 200, 73, 212, 213, 216, 244, 247, 185, 257

[56] References Cited

U.S. PATENT DOCUMENTS

| | | | |
|---|---|---|---|
| 39,662 | 8/1863 | Lockwood | 604/213 |
| 3,263,874 | 8/1966 | Porter et al. | 222/541 X |
| 3,986,509 | 10/1976 | Sneider | 604/213 |
| 4,112,942 | 9/1978 | Scaife | 604/244 X |
| 4,200,097 | 4/1980 | Hobbs, Jr. et al. | 604/213 |
| 4,217,988 | 8/1980 | Mills et al. | 222/541 X |
| 4,901,873 | 2/1990 | Weiler | 215/32 |

FOREIGN PATENT DOCUMENTS

58-166342 11/1983 Japan .
61-21075  1/1986 Japan .
61-200051 12/1986 Japan .
61-200052 12/1986 Japan .
1-140960  9/1989 Japan .

*Primary Examiner*—John D. Yasko
*Assistant Examiner*—Adam J. Cermak
*Attorney, Agent, or Firm*—Lowe, Price, LeBlanc & Becker

[57] ABSTRACT

A liquid container comprises a container body (2) having an opening (12) and a liquid-containing portion (2a), the container body containing liquid (W) therein; a cap (3) integrally formed with or fixedly connected to the opening after the liquid is charged in the container body, the cap having a base portion (3a) continuous to the opening, a thin-wall portion (3b) continuous to the base portion, a top portion (3c) continuous to the thin-wall portion, and at least one horn plate portion (13) continuous to the top portion, the horn portion radially outwardly extending beyond the diameter of the top portion; a cap opener (5) provided around the cap to be rotatable with respect to the cap, the cap opener having at least one craw plate (15) radially inwardly extending from inner wall of the cap opener to be in contact with the horn plate when the cap opener is rotated, an opening (5d) being made in the cap opener so as to exhaust the liquid (W) therethrough after the thin-wall portion is cut by twisting the cap opener relative to the cap. With this structure, leakage of liquid is effectively prevented.

3 Claims, 3 Drawing Sheets

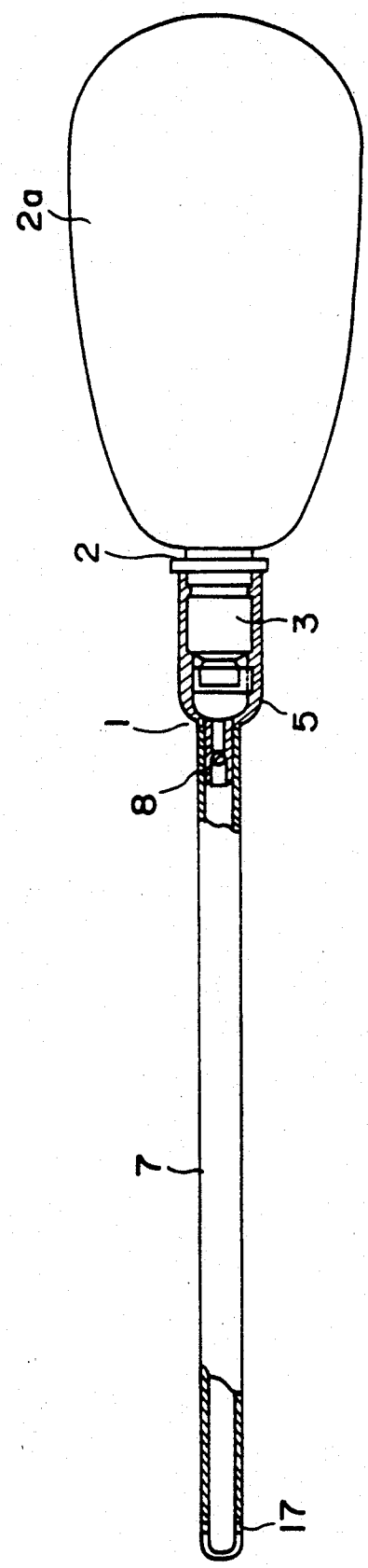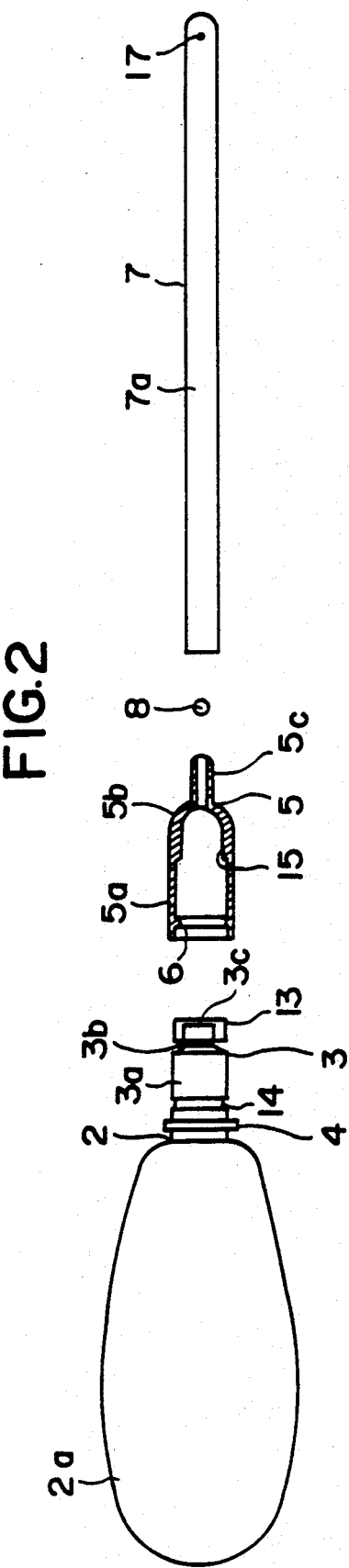

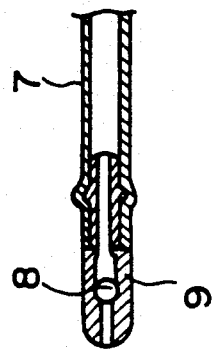
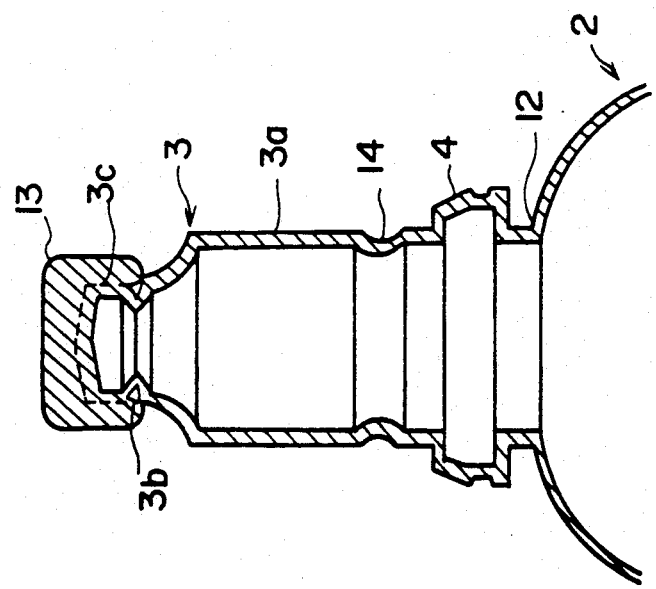
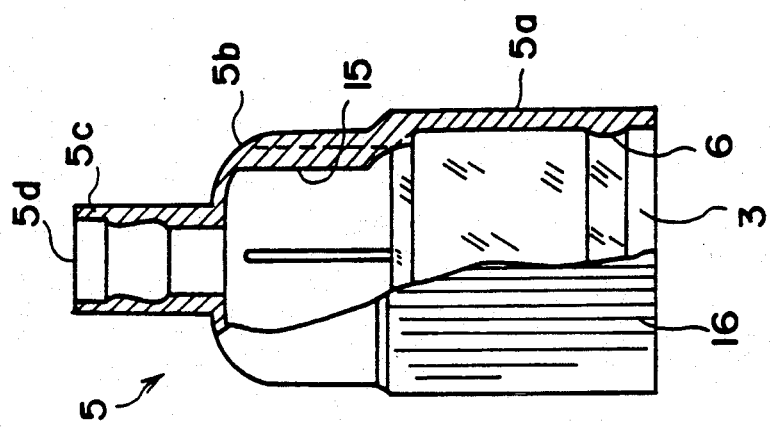

LIQUID CHEMICALS INJECTOR HAVING A LIQUID CONTAINER AND CATHETER

BACKGROUND OF THE INVENTION

1. Field of the Invention

This invention generally relates to a liquid container, and more particularly to an injection device for injecting liquid chemicals into a human or animal body by pressing or squeezing a deformable container.

2. Description of the Prior Art

In a known injector for enema of the type arranged to inject liquid chemicals into human or animal body by pressing a deformable container body, a check valve is provided for preventing liquid chemicals injected into intestine from flowing backward due to intestinal pressure as disclosed in Japanese Utility Model Publication (Koukoku) No. 61-21075.

Furthermore, in a device for enema having a catheter telescopically inserted into a tip portion of a container body containing liquid chemicals and a nozzle is provided at the tip portion of the catheter where a check valve is provided for preventing reverse flow of the injected liquid, a charging inlet is made at the tail portion of the container body for charging liquid chemicals into the container body and then the charging inlet is closed. Such as device is disclosed in Japanese Utility Model Provisional Publication No. 61-200052.

As described in the above, conventional devices for enema are arranged such that a catheter is telescopically inserted into an opening of the container body, and a cap is telescopically engaged with a nozzle attached to the tip of the catheter so as to close the nozzle by the cap. Therefore, there is a problem of leakage of liquid chemicals from the telescopically inserted portions between the container body and the catheter or between the nozzle and the cap before the device is actually used due to vibrations, temperature change or the like.

Furthermore, when inserting the nozzle into a human body, it is necessary that the catheter is bent so that the nozzle extends upwardly to prevent the leakage of the liquid chemicals.

SUMMARY OF THE INVENTION

The present invention has been made in view of the drawbacks of the conventional devices, and an object of the present invention is to provide a liquid container which is free from leakage problem caused from vibrations, temperature change or the like.

Another object of the present invention is to provide a liquid chemicals injector with a catheter which is readily handled by inserting the catheter into a human body without the problem of leakage.

According to the present invention there is provided a liquid container comprising: a container body having an opening and a liquid-containing portion, said container body containing liquid therein; a cap integrally formed with or fixedly connected to said opening after said liquid is charged in said container body, said cap having a base portion continuous to said opening, a thin-wall portion continuous to said base portion, a top portion continuous to said thin-wall portion, and at least one horn plate portion continuous to said top portion, said horn plate portion radially outwardly extending beyond the diameter of said top portion; and a cap opener provided around said cap to be rotatable with respect to said cap, said cap opener having at least one craw plate radially inwardly extending from inner wall of said cap opener to be in contact with said horn plate portion when said cap opener is rotated, an opening being made in said cap opener so as to exhaust said liquid therethrough after said thin-wall portion is cut by twisting said cap opener relative to said cap.

According to the present invention there is also provided a liquid chemicals injector comprising: the above-mentioned liquid container, said liquid-containing portion of said liquid container body is deformable; and a catheter telescopically inserted into said opening of said cap opener.

BRIEF DESCRIPTION OF THE DRAWINGS

The object and features of the present invention will become more readily apparent from the following detailed description taken in conjunction with the accompanying drawings in which:

FIG. 1 is a partial cross sectional view of an embodiment of the liquid chemicals injector according to the present invention;

FIG. 2 is an exploded view of the embodiment shown in FIG. 1;

FIG. 6 is a partial cross-sectional view of a cap opener shown in FIGS. 1 and 2;

FIG. 7 is a partial cross-sectional view of the cap shown in FIGS. 1, 2 and 5; and FIG. 8 is a cross-sectional view of a nozzle used in another embodiment of the present invention.

The same or corresponding elements or parts are designated at like references throughout the drawings.

DETAILED DESCRIPTION OF THE INVENTION

Figure 5:
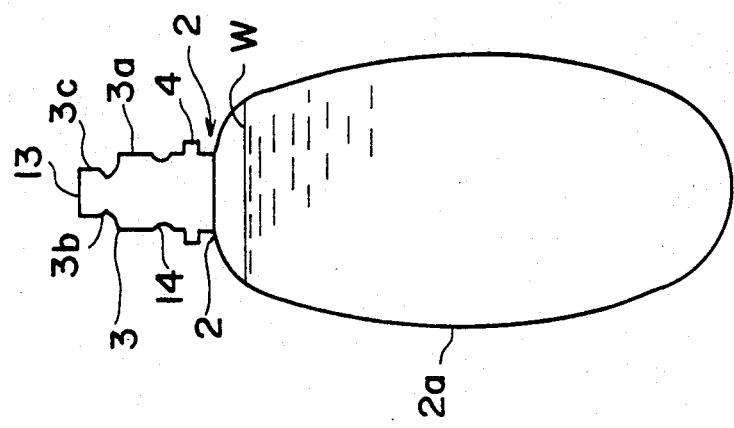
FIG. 5 is a side view of the container body shown in FIGS. 3 and 4 showing a state after a cap is attached thereto.

Referring now to the attached drawings, an embodiment of the liquid chemicals injector according to the present invention will be described.

As shown in a partial cross-sectional view of FIG. 1, the liquid chemicals injector, which is an enema injector, generally designated at numeral 1 generally comprises a liquid container body 2 in which liquid chemicals W are charged, a cap 3 attached to the container body 2, a cap opener 5 for opening the cap 3, a catheter 7 telescopically inserted into an opening 5c of the cap opener 5. A check valve 8 is preferably provided for preventing reverse flow of the liquid chemicals W, and in this embodiment, the check valve 8 is provided in the opening 5c of the cap opener 5.

Figure 3:
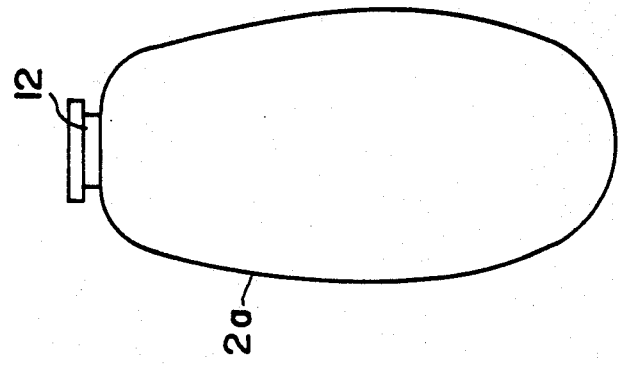
FIG. 3 is a side view of a container body shown in FIGS. 1 and 2 showing a state before a cap is attached thereto.

The liquid container body 2 comprises a liquid-containing portion 2a and an opening 12 as seen in FIG. 3. The liquid-containing portion 2a is deformable by a stress of a user's hand so that the liquid chemicals therein are exhausted. However, when the liquid container 2 is used for just containing and keep liquid therein, the liquid-containing portion 2a is not necessarily required to be deformable.

In this embodiment, the opening 12 is used as a charging inlet through which the liquid chemicals W are charged into the liquid-containing portion 2a. After the liquid chemicals are charged into the liquid-containing portion 2a, the cap 3 is either integrally formed with the opening 12 or fixedly attached to the opening 12 through welding. Integral formation of the cap 3 immediately after charging of the liquid chemicals is known as bottle packing method. In this way the liquid chemicals, such as enema, is charged into the container body 2 and the cap 3 is attached or formed to hermetically seal the opening 12.

Figure 4:
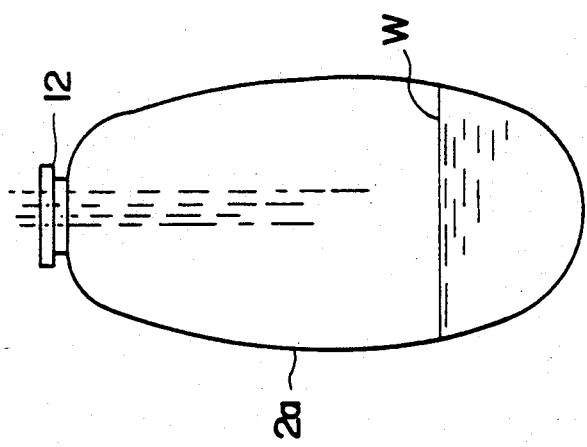
FIG. 4 is a schematic side view of the container body shown in FIG. 3, showing charging of liquid chemicals.

The cap 3 has the following structure so that a given portion of the cap 3 is cut or broken when it is intended to discharge or exhaust the liquid chemicals. The cap 3 comprises a generally hollow cylindrical base portion 3a continuous to the opening 12 as best seen in FIG. 7, a thin-wall portion 3b continuous to the base portion 3a, a top portion 3c continuous to the thin-wall portion 3b, and at least one horn plate 13 portion continuous to the top portion 3c. The horn plate portion 13 radially outwardly extends beyond the diameter of the top portion 3c. This horn plate portion 13 will be used for receiving twisting force from the cap opener as will be described hereinlater so as to cut the cap 3 at the thin-wall portion 3b. The top portion 3c has a closed end and is integrally formed with the remaining parts of the cap 3. The cap 3 is made of a soft synthetic resin, such as a polyethylene resin. The container body 2 may also be made of the same resin as that of the cap 3. As seen in FIGS. 4 and 7, the cap 3 also has a flange portion 4 at its base portion 3a in the vicinity of the opening 12 and an annular groove 14 near the flange portion 4 opposite to the opening 12.

The cap opener 5 is rotatably provided with respect to the cap 3 as shown in FIGS. 1 and 6. More specifically, the cap opener 5 is generally bell or dome shaped to telescopically engage the outer periphery of the cap 3. The cap opener 5 comprises a hollow cylindrical wall portion 5a engaging the base portion 3a of the cap 3, a dome-like wall portion 5b continuous to the hollow cylindrical wall portion 5a, and a mouth portion 5c continuous to the dome-like wall portion 5b. The mouth portion 5c is arranged at the summit of the dome-like wall portion 5b and has an opening 5d at its center. On an inner wall of the hollow cylindrical wall portion 5a, provided is an annular projecting ring portion 6 which engages the annular groove 14 of the cap 3 when the cap opener is assembled with the cap 3. With the engagement between the projecting ring portion 6 and the annular groove 14, the cap opener 5 is rotatable about the axis of the cap 3 relative to the cap 3, and is prevented from being detached from the cap 3. On an inner wall of the dome-like wall portion 5b, provided is at least one craw plate 15 which radially inwardly extends from the inner wall. As seen in FIG. 2, two craw plates 15 are provided in this embodiment. The shape and size of the craw plate 15 are designed so that the craw plate 15 comes into contact with the horn plate portion 14 when the cap opener 5 is rotated by a given angle. The cap opener 5 is made of a hard synthetic resin, such as olefin resin. In this embodiment, a check valve 8 is inserted into and held in the mouth portion 5c. On the outer periphery of the hollow cylindrical wall portion 5a, provided is a non-slip portion 16 where the surface is undulatory. In order to keep tightness between the cap 3 and the cap opener 5, a suitable sealing member, such as an O-ring may be provided around the groove 14 if necessary.

Although only a single horn plate portion 13 and a pair of craw plates 15 are provided in the above embodiment, the number of these members may be selected as discussed below to provide a non-engagable degree of rotational angle of the cap opener 5 relative to the cap 3.

When the number of craw plates 15 provided to the inner wall of the dome-like wall portion 5b is 2 or 1, then it is desired to provide two or more horn plate portions 3 to the top portion 3c of the cap 3. On the other hand, when number of horn plate portions 13 is 2 or more, then it is desired to provide two or one craw plate 15 to the top portion 3c.

The catheter 7 having an elongate tube portion 7a and a closed end at its top is telescopically engaged with the mouth portion 5c of the cap opener 5 at its base portion. One or more small openings 17 are made in the vicinity of the closed end for discharging the liquid chemicals lead through the catheter 17 after the cap 3 is cut. The catheter 17 is preferably made of a soft synthetic resin, such as vinyl chloride, latex or the like to be bendable.

One or more of the container body 2, the cap 3, the cap opener 5, and the catheter 7 may be made of a transparent synthetic resin so that the residual amount of the liquid chemicals W and or state of injection may be watched with the eye. Furthermore, when the cap opener 5 is made of a transparent synthetic resin, the cut state of the cap 3 can be seen.

FIG. 8 shows another embodiment of the liquid chemicals injector according to the present invention, and this embodiment differs from the first embodiment shown in FIGS. 1 to 7 in that the check valve 8 is inserted in and held in a nozzle 9 telescopically attached to the tip portion of a catheter 7.

The liquid chemicals injector according to the present invention will be used as follows for injecting liquid chemicals of enema into human or animal body as follows:

At first, the liquid-containing portion 2a of the container body 2 is held by one hand, and the tip portion of the catheter 7 is lead to be inserted into anus by the other hand. Then the cylindrical wall portion 5a of the cap opener 5 is held by the other hand to rotate the same to the left or right. As a result the cap opener 5 rotates about the axis of the cap 3 so that the craw plate 15 provided to the dome-like wall 5b comes into contact with the horn plate portion 14 extending from the top portion 3c of the cap 3. As the cap opener 5 is further rotated, the top portion 3c is twisted relative to the base portion 3a. When torsional stress applied to top portion 3c exceeds a given value, the thin-wall portion 3b is cut so that the top portion 3c is partially or entirely detached from the base portion 3a. The cutting state of the top portion 3c of the cap 3 depends on the material of the cap 3, the thickness of the thin-wall portion 3b or the like, it is desirable that the top portion 3c can be detached from the base portion when the cap opener 5 is rotated by approximately 60 to 180 degrees.

After the top portion 3c is detached from the base portion 3a, the liquid-containing portion 2a is depressed or squeezed by the holding hand, the liquid chemicals contained in the container body 2 are lead through the cap 3, the cap opener 5, and the catheter 7 into intestine.

As the liquid chemicals injector according to the present invention has the above-described structure, the following advantageous effect are obtained:

Since the cap 3 is either integrally formed with or fixedly attached to the opening 12 with liquid chemicals being charged into the container body 2 after the liquid-containing portion 2a and the opening 12 are formed, the forming of the liquid container 2, charging of the liquid chemicals W and sealing of the opening 12 are may be sequentially performed with less steps when compared to the conventional production steps. Furthermore, there is no need to add antiseptic to the liquid chemicals. Since the liquid chemicals are hermetically sealed until the top portion 3c of the cap 3 is twisted and detached with the rotation of the cap opener 5 after the catheter 7 is inserted into a human body, leakage of the liquid chemicals can be perfectly prevented in transportation phase and also before the insertion of the catheter into intestine.

Although the top portion 3c of the cap is continuous to the base portion 3a via the thin-wall portion 3b which is cuttable or breakable, this thin-wall portion 3b is never twisted to be detached from the base portion unless the cap opener 5 is twisted since the cap 3 is entirely covered by cap opener 5. On the contrary, as the cap opener 5 is rotated relative to the cap 3 when it is intended to discharge or exhaust the liquid chemicals to inject the same into intestine, the thin-wall portion 3b can be readily cut in receipt of twisting stress through the contact between the craw plate 15 and the horn plate portion 13. In this way, the cap 3 can be easily opened with the rotation of the cap opener 5. The top portion 3c detached from the base portion 3a remains in the cap opener 5, but the top portion 3c would not be an obstacle for the injection of the liquid chemicals. As a result, the liquid chemicals can be injected into intestine in the same manner as in a conventional injector as the liquid-containing portion 2a is depressed.

The invention has been described in connection with particular embodiments, and various modifications and changes may be made without departing from the scope of the invention defined by the following claims.

What is claimed is:

1. A liquid chemicals injector comprising:
   (a) a liquid container having
      (i) a container body including an opening and a deformable liquid-containing portion, said container body containing a liquid therein,
      (ii) a cap integrally formed with or fixedly connected to said opening after said liquid is charged in said container body, said cap having a base portion continuous to said opening, a thin-wall portion continuous to said base portion, a top portion having a diameter and being continuous to said thin-wall portion, and at least one horn plate portion extending radially outwardly beyond the diameter of said top portion, and
      (iii) a cap opener provided around and being rotatable with respect to said cap, said cap opener having at least one craw plate extending radially inwardly from an inner wall of said cap opener to be in contact with said horn plate portion when said cap opener is rotated, an opening being formed in said cap opener after twisting said cap opener relative to said cap and thereby cutting said thin-wall portion, said opening allowing exhaust of said liquid therethrough; and
   (b) a catheter telescopically engaged with said opening of said container.

2. A liquids chemical injector as claimed in claim 1, further comprising a check valve in said opening of said cap.

3. A liquids chemical injector as claimed in claim 1, further comprising a check valve in said catheter.

* * * * *